(12) United States Patent
Rajagopalan et al.

(10) Patent No.: US 8,483,973 B2
(45) Date of Patent: Jul. 9, 2013

(54) DEVICE FOR MEASURING THE PURITY OF ULTRAPURE WATER

(75) Inventors: Pascal Rajagopalan, Aulnay-Sous-Bois (FR); Antony Vanheghe, Asnieres sur Seine (FR); Celine Le Ninivin, Verneuil sur Seine (FR); Aristotelis Dimitrakopoulos, Saint Martin de Nigelles (FR)

(73) Assignee: EMD Millipore Corporation, Billerica, MA (US)

( * ) Notice: Subject to any disclaimer, the term of this patent is extended or adjusted under 35 U.S.C. 154(b) by 477 days.

(21) Appl. No.: 12/455,418

(22) Filed: Jun. 2, 2009

(65) Prior Publication Data

US 2009/0319194 A1    Dec. 24, 2009

(30) Foreign Application Priority Data

Jun. 6, 2008   (FR) ...................... 08 53787

(51) Int. Cl.
*G01N 33/50* (2006.01)
*B01J 49/00* (2006.01)

(52) U.S. Cl.
USPC ............................................ 702/23; 210/96.1

(58) Field of Classification Search
USPC ................. 703/23; 210/96.1, 202, 205, 266, 210/136, 748.1, 198.1, 746, 130, 254
See application file for complete search history.

(56) References Cited

U.S. PATENT DOCUMENTS

| | | | | |
|---|---|---|---|---|
| 4,691,168 A | | 9/1987 | Dzula | 324/439 |
| 5,272,091 A | * | 12/1993 | Egozy et al. | 436/146 |
| 5,518,608 A | | 5/1996 | Chubachi | 210/96.1 |
| 5,868,924 A | * | 2/1999 | Nachtman et al. | 210/85 |
| 7,057,400 B2 | | 6/2006 | Gaignet | |
| 8,179,141 B2 | | 5/2012 | Rajagopalan et al. | |
| 2004/0112829 A1 | * | 6/2004 | Jenkins et al. | 210/614 |
| 2005/0165575 A1 | | 7/2005 | Mettes | |
| 2011/0068812 A1 | | 3/2011 | Rajagopalan et al. | |

FOREIGN PATENT DOCUMENTS

| | | |
|---|---|---|
| EP | 0 498 888 | 8/1992 |
| EP | 0 581 157 | 2/1994 |
| WO | 2007/053515 A1 | 5/2007 |

OTHER PUBLICATIONS

French Search Report dated Jan. 16, 2009.
Light, et al, "The Fundamental Conductivity and Resistivity of Water", Electrochemical and Solid-State Letters, 8 (1) E16-E19 (2005) XP-002511049.
International Search Report dated Oct. 21, 2009.
Office Action mailed Mar. 25, 2013 in co-pending U.S. Appl. No. 12/994,208.

\* cited by examiner

*Primary Examiner* — Alexander H Taningco
*Assistant Examiner* — Manuel Rivera Vargas
(74) *Attorney, Agent, or Firm* — Nields, Lemack & Frame, LLC

(57) ABSTRACT

Disclosed is a device for analyzing the quantity of organic compounds existing in a liquid, such as ultrapure water, at the outlet from a purification device including in series a filter, an oxidizing device and a polishing device, and further including a resistivity measuring device for measuring the resistivity of water to determine the purity thereof. Only one resistivity measuring cell is used, and the outlet points of the filter and the oxidizing device are connected to the resistivity measuring cell by pipes provided with an analysis valve and/or check valves selectively enabling circulation of the liquid within them.

6 Claims, 2 Drawing Sheets

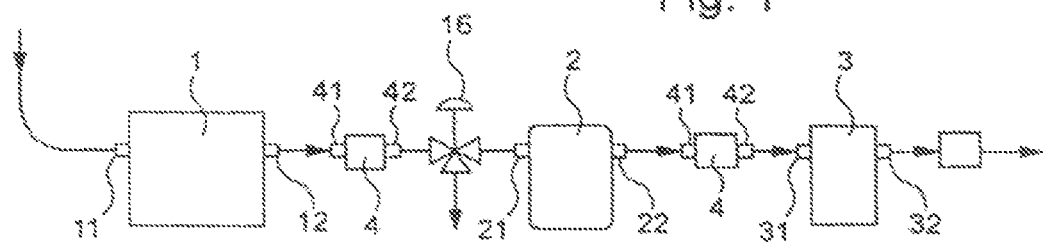
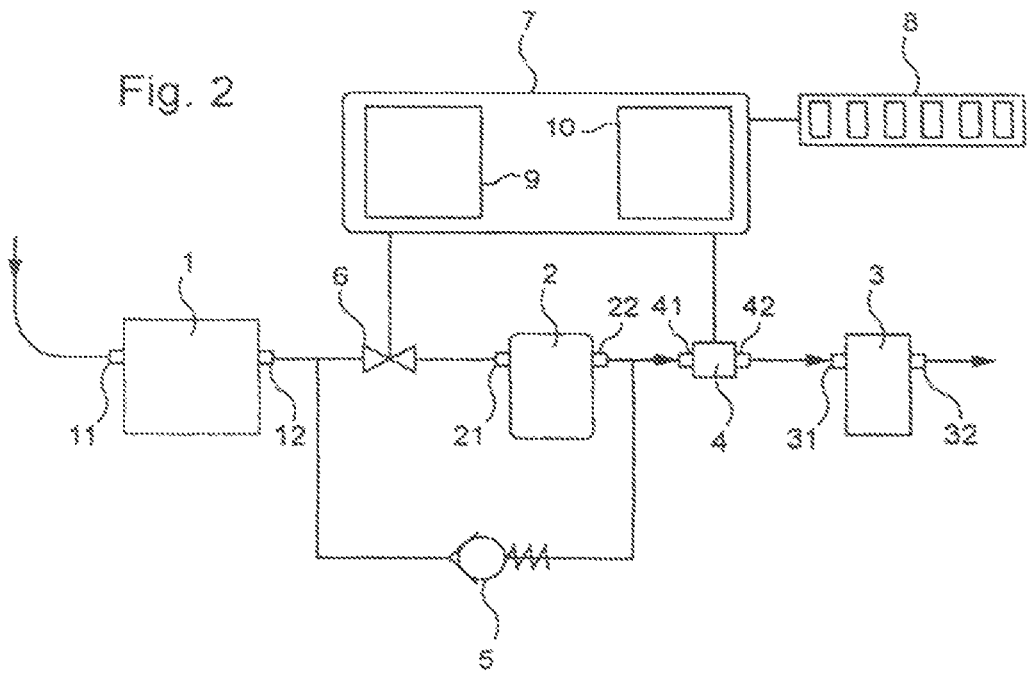

DEVICE FOR MEASURING THE PURITY OF ULTRAPURE WATER

The invention relates to a device for analyzing the level of purity of a liquid obtained after purification treatment and in particular that of so-called ultrapure water (less than 10 parts per billion (ppb)) implementing that method.

The method generally employed for purifying water, or any other liquid, begins with passage through a first device including filtration and purification means, of the type activated carbon filtering, ion exchange resin filtering or reverse osmosis filtering. At the outlet of the first treatment means, the ultrapure water contains very few ions and is characterized by a resistivity close to, or even equal to, 18.2 MΩ·cm, but still contains organic compounds. It is then passed through a second device in which those organic compounds are oxidized in order to ionize them. During this oxidation the organic compounds are degraded and the atoms of carbon are then present in the form of carbon dioxide gas, which is dissolved in water to form bicarbonate ions $HCO3^-$. This oxidation is obtained by passage in front of an ultraviolet lamp or by adding hydrogen peroxide.

The third purification step consists in polishing the water, i.e. passing it through an ion exchange resin that blocks the ions created during the preceding step and thus completes the purification of the water. During this step the organic compounds that were not degraded during the oxidation phase are not affected.

It remains to determine the purity of the water obtained at the end of this process. One method commonly employed measures its resistivity at the outlet from the oxidation means, which is directly linked to the dissolved carbon dioxide gas content, i.e. to the number of bicarbonate ions, and then determines the resistivity that it would have if the oxidation process had been continued until the end, i.e. if all its organic compounds had been degraded. This process, necessitating an infinite time period, can obviously not be used and it is therefore necessary to employ methods of estimating this limit resistivity.

There is already known, in particular from the Millipore Corporation patent EP0581157, a device and a method for analyzing the purity of water that utilize the difference in the resistivity of the water between the upstream and downstream sides of the oxidation means to estimate this resistivity at infinity. This method uses the device in a first or reference mode to measure the resistivity difference between the upstream side and the downstream side of the oxidation means on water samples that have been exposed for various times to the oxidation means. The exposure times are typically of the order of 10, 20, 30, 40, 50 and 60 seconds. By extrapolation from the curve obtained, it is possible to determine what the resistivity of the water obtained would be after an infinite exposure time, i.e. if all the carbon atoms were to be degraded. Using an appropriate modeling program, such as the MINTEQA2 program described in the publication EPA/600/3-91/021 (1991) of the US Environmental Protection Agency, it is possible to determine from the resistivity at infinity the total organic carbon (TOC) content in the reference water.

A second or purification or analysis mode is then used during which ultrapure water is passed at a given flowrate through oxidation means to determine its content of organic compound impurities and thus to verify that its purity remains nominal. The resistivity difference between the upstream and downstream sides of the oxidation means is measured continuously and the total quantity of organic compounds is deduced therefrom by means of an assumed linear relationship between the resistivity difference measured in the purification mode and the resistivity difference at infinity estimated in the reference mode.

The invention aims to propose a device for analyzing the quantity of organic compounds existing in a liquid at the outlet from a purification device that is more economical and easier to use.

To this end the device of the invention for analyzing the quantity of organic compounds existing in a liquid, such as ultrapure water, at the outlet from a purification device including in series filter means, oxidation means and polishing means, further includes means for measuring the resistivity of water to determine the purity thereof, it is characterized in that said measuring means include only one resistivity measuring is cell and in that connecting means and fluid circulation control means are provided that are adapted to:
  prohibit circulation of the fluid between the outlet point of the filter means and the inlet point of the oxidation means whilst authorizing circulation of the fluid between the outlet point of the filter means and the inlet point of the resistivity measuring cell, or
  authorize circulation of the fluid between the outlet point of the filter means and the inlet point of the oxidation means whilst prohibiting circulation of the fluid between the outlet point of the filter means and the inlet point of the resistivity measuring cell.

The reduction to a single cell avoids the problems of uncertainty encountered, notably when the calculation uses the value of the difference between a number of cells, and most importantly reduces costs since, given their complexity, these cells account for a large part of the overall cost of the device.

According to preferred features, intended to simplify the production of the liquid circuit:
  said resistivity measuring cell is positioned in series in the circuit between the outlet point of the oxidation means and the inlet point of the polishing means;
  outlet point of the filter means is connected to said resistivity cell by a branch circuit comprising a check valve that is open only if the pressure at the inlet reaches a predefined value;
  the outlet point of the filter means is connected to the inlet point of the oxidation means by a simple analysis valve with two positions, open and closed;
  the two-position valve is situated on the downstream side of the starting point of the branch circuit;
  the analysis valve and the measuring means are connected to a control and calculation unit including a control module adapted to command opening and closing of the analysis valve in a predefined sequence and a calculation module adapted to collect the resistivity value from said measuring cell to deduce the purity of the water therefrom in real time.

The disclosure of the invention continues next with the description of a preferred embodiment given hereinafter by way of nonlimiting illustration and with reference to the appended drawings. In the drawings:

FIG. 1 is a diagram of a prior art water purification device;

FIG. 2 is a diagram of a water purification device of one embodiment of the invention;

Figure 3:
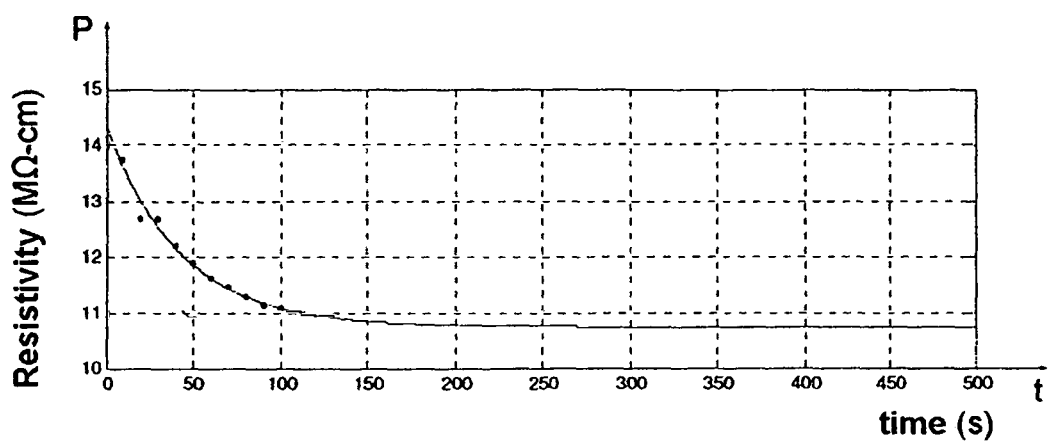
Figure 4:
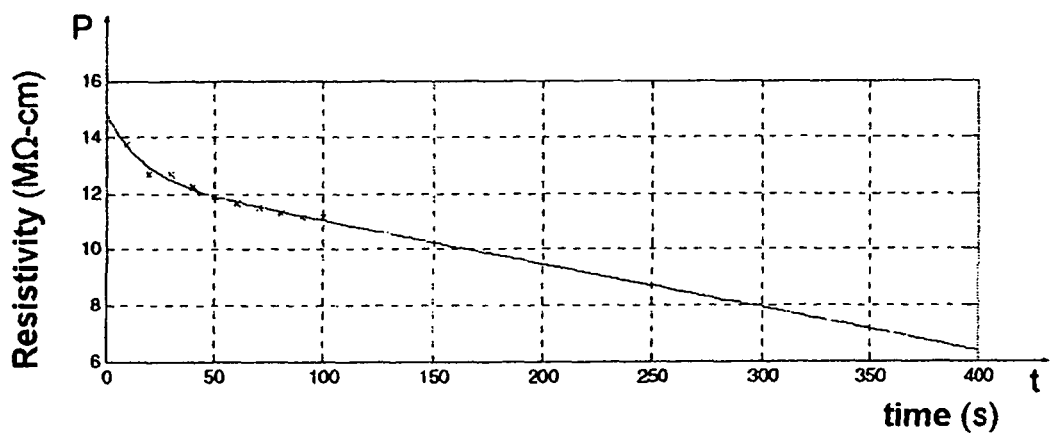

FIG. 3 is a curve representing the decrease of the resistivity of the water from any value, in the reference mode, as a function of the time spent in the reactor, using a prior art approximation method; and FIG. 4 is a curve representing the decrease of the resistivity of the water from any value, in the reference mode, as a function of the time spent in the reactor, using an approximation method for the invention.

FIG. 1 shows a prior art water purification device comprising, in series, filter means 1, oxidation means 2 and water polishing means 3. Two cells for measuring the resistivity of the water 4 are inserted into the circuit respectively at the outlet of the filter means 1 and at the outlet of the oxidation means 2.

The filter means 1 typically consist of filters based on activated carbon such as those marketed by the company Millipore Corporation under the trade mark Q-GARD®. At the outlet of these filter means the water has a purity of approximately 10 ppb and a resistivity close to or equal to 18.2 MΩ·cm.

Here the oxidation means 2 consist of a mercury vapor UV lamp radiating in the range from 185 to 254 nanometers. The water that flows through the purification device is exposed to this radiation for time periods from 2 to 120 seconds.

The polishing means 3 typically consist of an ion exchange resin and produce water with a final purity of the order of 1 to 5 ppb.

Water enters the device through the inlet point 11 of the filter means. The outlet point 12 of the filter means is connected by a pipe to the inlet point 41 of the first resistivity cell 4, the outlet of which is connected to a three-way valve 16. This three-way valve 16 is connected on the one hand to the inlet point 21 of the oxidation means and on the other hand to an evacuation circuit (not shown). It causes water leaving the filter means to enter the oxidation means 2 or evacuates it from the circuit.

The outlet point of the oxidation means 22 is connected by a pipe to the inlet point 41 of the second resistivity cell 4, the outlet point 42 of which is itself connected to the inlet point 31 of the polishing means. The ultrapure water obtained is then available at the outlet point 32 of the polishing means.

FIG. 2 shows a water purification device of one embodiment of the invention, comprising in series as above filter means 1, oxidation means 2 and water polishing means 3. This circuit differs from the prior art circuit in that it includes only one measuring cell 4, placed in series between the outlet point 22 of the oxidation means 2 and the inlet point 31 of the polishing means 3, and in that the three-way valve 16 is replaced by a simple analysis valve 6 with two positions, open and closed, that is less costly and easier to use.

Water at the outlet of the filter means is divided between two pipes, one of which goes to the analysis is valve 6, as above, and a second of which, forming a bypass circuit, goes directly to the resistivity measuring cell 4 via a check valve 5 calibrated to open above a certain value.

Water from the filter means 1 is directed, entirely by action on the analysis valve 6, either to the oxidation means 2 or directly to the measuring cell 4 via the branch circuit equipped with the check valve 5. When the analysis valve 6 is in the open position, it allows liquid to pass to the oxidation means; the pressure in the branch circuit falls and the check valve 5 remains closed. If the analysis valve 6 is closed, the pressure rises in the branch circuit and the check valve 5 opens, allowing water to pass to the resistivity measuring cell 4.

FIG. 2 also shows control means for the water purification device, which include a control and calculation unit 7 and a display device 8 adapted to provide the operator in real time with information on the purity level obtained. This control and calculation unit 7 controls the position of the analysis valve 6 by means of a control module 9 and processes information supplied by the resistivity measuring cell 4 in a calculation module 10. The calculation module 10 executes the water purity calculation method and transmits the result obtained to the display device 8.

As in the prior art, the method for measuring the purity of water comprises a first measurement of the resistivity of the water at the outlet of the filter means followed by the use of two distinct operating modes of the purification device, a reference mode and an analysis mode. To evaluate the resistivity of the water supplied by the filter means 1, the analysis valve 6 is closed and the pressure on the upstream side of the check valve increases; the valve opens when the pressure reaches the nominal opening value and the flow of liquid circulates in the branch circuit via the check valve 5. In analysis mode or in reference mode, when the analysis valve is open, the check valve 5 prevents circulation of the liquid in the branch circuit, the pressure at its inlet remaining below the nominal opening pressure. The analysis valve is open continuously in analysis mode. In reference mode, however, it remains closed during predetermined time periods during which the water situated in the oxidation means continues to be exposed to the UV radiation. The analysis valve is then opened to send irradiated water to the measuring cell 4. Thanks to the significantly different time periods, the reference module determines the evolution of the resistivity of the water as a function of the time it has spent in the oxidation means.

The configuration with a check valve 5 and an analysis valve 6 means that a single measuring cell 4 can be used to measure the resistivity at the outlet of the filter means 1 and at the outlet of the oxidation means 2. This is reflected firstly in a major saving in the cost of producing the device and secondly by greater ease of use, the three-way valves of the prior art being complicated to use under the hydraulic operating conditions of the device.

FIG. 3 shows a number of points indicating the resistivity of the water at the outlet of the oxidation means 2 as a function of the time that it has spent in those means. FIG. 3 also gives a curve approximating those points by an exponential function of the type $\rho(t)=\rho_\infty+(\rho_0-\rho_\infty)\,e^{-t/T}$. FIG. 4 gives the resistivity value of the same points and an approximation curve produced by a mixed (exponential and linear) function, which can be represented as follows:

$$\rho(t)=\rho_\infty+(\rho_0-\rho_\infty)e^{-t/T}+\rho_{slope}t+\rho_{intercept})\cdot u_{start,length}(t)$$

where $\rho_{slope}$ and $\rho_{intercept}$ are the slope and the ordinate at the origin of a linear function and $u_{start,length}(t)$ is a function having the value 0 on a first portion of the abscissa axis corresponding to a purely exponential function and a value of 1 for the remainder of the abscissa axis where the function can be treated as the sum of an exponential function and a linear function.

The FIG. 4 curve is a better approximation of the evolution of the resistivity as a function of the UV irradiation time, especially if the UV reactor has plastic material parts that are in contact with the water and are subjected to this radiation. The linear part of the curve takes into account the presence in the water of organic compounds that are generated by the photo-ionization of these materials or by dissolving carbon dioxide gas from the atmosphere. This new approximation curve reduces by 50% the adjustment effected using the least-squares method.

The process leading to measurement of the purity of the water obtained after it passes through the purification device is described next.

The first operation is to measure the resistivity of the water at the outlet of the filter means 1, by closing the analysis valve 6. The water then flows via the branch circuit and the check valve 5 directly into the resistivity measuring cell 4, which gives the value of the resistivity of the water at the outlet of the filter means 1. This value $\rho_{UPW}$ remains a priori constant throughout the purification operation as, it depends only on characteristics of the liquid before purification.

Next a series of operations in a so-called reference mode begins. The aim of this mode is to determine the resistivity at infinity $\rho_{\infty REF}$ of water that will serve as a reference fluid for the remainder of the measurements. The analysis valve 6 is open briefly, for the time to replace water present in the oxidation means with new water coming from the filter means, after which this analysis valve 6 is closed. This valve remains closed for a particular first time period and is then opened so that water retained in the oxidation means passes into the resistivity measuring cell 4; the resistivity value of this water is recorded and then the same operation is started again, varying the time spent by the water in the oxidation means. There is obtained in this way a series of measurements of resistivity as a function of time and regression techniques are used to deduce the best approximation curve passing through these points in a diagram giving the resistivity as a function of time. There is then obtained the resolution of the parameters of the function $\rho(t)=\rho_{\infty REF}+(\rho_0-\rho_{\infty REF})\ e^{-t/T}+\rho_{slope}\ t+\rho_{intercept})\cdot u_{start,length}(t)$, which were unknown until now, i.e. the parameters $\rho_{\infty REF}$, $\rho_0$, T, $\rho_{slope}$, $\rho_{intercept}$ and the cut-off point of the function $u_{start,length}$. This function with six unknown parameters makes it necessary to carry out experiments with at least six different durations. This determines in particular the parameter $\rho_{\infty REF}$ which gives the value of the resistivity that the water would have if it had remained an infinite time in the oxidation means, in other words if all its organic components had been degraded into bicarbonate ions.

The knowledge of these two values (values $\rho_{UPW}$ of the resistivity at the outlet of the filter means and value $\rho_{\infty REF}$ of the resistivity at infinity after complete oxidation) provide for starting the phase of analyzing the water coming from the purification device and of knowing at all times its concentration in carbon atoms, i.e. its purity level. To this end the analysis valve is left open continuously.

Water that has passed through the filter means passes with a given flowrate through the oxidation means where it is subject to partial degradation of its organic components and where its resistivity evolves because of the dissolution of the carbon dioxide gas generated in this way. At the outlet of the oxidation means its resistivity p is measured by the measuring cell 4 and is a function of the residence time t during which it continued to be exposed to irradiation by the oxidation means 2.

Taking the single exponential curve for the resistivity evolution model, we can write $\rho(t)=\rho_{\infty}+(\rho_{UPW}-\rho_{\infty})\ e^{-t/T}$. The approximation, applied here, which consists in retaining only the exponential part of the curve for the evolution of resistivity as a function of time and that could not have been taken into account in the reference mode with reactors including plastic material parts, is acceptable here because the exposure times of the water in the UV reactor remain short, which was not the case in the reference mode.

The value to be determined next is the value $\rho_{\infty}$ that is used to obtain the purity of the water at the outlet from the purification device. This parameter is calculated by an analytical extrapolation method explained below.

Designating by $k_{\alpha}$ the ratio between the terms $\rho(t)$ and $\rho_{\infty}$ and by $e^{-\alpha}$ the formula $e^{-t/T}$, for simplicity, we obtain:

$$1/k_{\alpha}=1+(\rho_{UPW}/\rho_{\infty}-1)e^{-\alpha}$$

By stating that this formula applies equally to the reference mode, in the left-hand portion of its curve ($u_{start,length}(t)=0$) for the same residence time, we obtain:

$$K_{REF}=\rho(t)_{REF}/\rho_{\infty REF},\ \text{and}$$

$$e^{-\alpha}=(1-K_{REF})/K_{REF}\times\rho_{\infty REF}/(\rho_{UPW}-\rho_{\infty REF})$$

It is then possible to express $k_{\alpha}$ as a function of $\rho_{\infty}$ and parameters that are known through using the reference mode ($K_{REF}$, $\rho_{UPW}$ and $\rho_{\infty REF}$).

Using the residence time t as a working parameter intended to tend toward infinity, it is possible, using a standard iterative method, to cause $k_{\alpha}$ and $\rho_{\infty}$ to evolve successively until the latter parameter converges.

There is obtained in this way the value of the resistivity that the water in the oxidation means would have if it had remained therein for an infinite time, i.e. if oxidation of its organic compounds had continued until complete.

Standard methods, for example that used by the MINT-EQA2 program, then work back from the value of the resistivity at infinity to the total organic carbon (TOC) content of the water, i.e. its purity expressed in ppb.

Numerous variants are possible as a function of circumstances, and in this regard it must be pointed out that the invention is not limited to the examples described and shown.

The invention claimed is:

1. Device for analyzing the quantity of organic compound existing in a fluid, at the outlet from a purification device including in series a filter, an oxidizer, a polisher and only one resistivity measuring cell and wherein a connector and fluid circulation controller are provided that operate in a first mode that:
   prohibits circulation of the fluid between the outlet point of said filter and the inlet point of said oxidizer whilst authorizing circulation of the fluid between the outlet point of said filter and the inlet point of said resistivity measuring cell; and operate in a second mode that
   authorizes circulation of the fluid between the outlet point of said filter and the inlet point of said oxidizer whilst prohibiting circulation of the fluid between the outlet point of said filter and the inlet point of said resistivity measuring cell.

2. Device according to claim 1 for analyzing the quantity of organic compounds existing in a liquid wherein the outlet point of said filter is connected to the inlet point of said oxidizer by a simple analysis valve with two positions, open and closed.

3. Device according to claim 2 for analyzing the quantity of organic compound existing in a liquid wherein the outlet point of said filter is connected to said resistivity cell by a branch circuit having a starting point, and wherein said simple analysis valve is situated on the downstream side of said starting point of said branch circuit.

4. Device according to claim 3 for analyzing the quantity of organic compounds existing in a liquid wherein said simple analysis valve and said resistivity measuring cell are connected to a control and calculation unit including a control module adapted to command opening and closing of said simple analysis valve in a predefined sequence and a calculation module adapted to collect the resistivity value from said measuring cell to deduce the purity of the water therefrom in real time.

5. Device according to claim 1 for analyzing the quantity of organic compounds existing in a liquid wherein said resistivity measuring cell is positioned in series in a circuit between the outlet point of said oxidizer and the inlet point of said polisher.

6. Device according to claim 1 for analyzing the quantity of organic compounds existing in a liquid wherein the outlet point of said filter is connected to said resistivity cell by a branch circuit comprising a check valve that is open only if the pressure at the inlet reaches a predefined value.

* * * * *